United States Patent [19]

Callahan et al.

[11] 4,001,256

[45] Jan. 4, 1977

[54] PYRIDYLALKYL PHENYL UREAS AND THEIR N-OXIDES

[75] Inventors: William A. Callahan; Eldridge Myles Glenn, both of Kalamazoo; Douglas L. Rector, Parchment, all of Mich.

[73] Assignee: The Upjohn Company, Kalamazoo, Mich.

[22] Filed: June 25, 1975

[21] Appl. No.: 590,031

Related U.S. Application Data

[63] Continuation-in-part of Ser. No. 428,361, Dec. 26, 1973, abandoned.

[52] U.S. Cl. .................. 260/295 E; 260/295.5 D; 424/263
[51] Int. Cl.² ..................................... C07D 213/38
[58] Field of Search ................ 260/295 E, 295.5 D

[56] References Cited

UNITED STATES PATENTS

| | | | |
|---|---|---|---|
| 3,128,280 | 4/1964 | Rorig | 260/349 |
| 3,700,678 | 10/1972 | Mihailovski | 260/295.5 D |

FOREIGN PATENTS OR APPLICATIONS

| | | | |
|---|---|---|---|
| 196,799 | 0000 | U.S.S.R. | 260/295 E |

OTHER PUBLICATIONS

Juby et al., J. Med. Chem. 10, pp. 491–495, (1967).

Sculley et al., J. Am. Chem. Soc., vol. 75, pp. 3400–3403, (1953).
Robison et al., J. Am. Chem. Soc. vol. 77, pp. 6554–6559, (1955).
Skinner et al., J. Org. Chem., vol. 25, pp. 2046–2047, (1960).
Novikov et al., Chemical Abstracts 70:77727v, (1969).

*Primary Examiner*—Norman A Drezin
*Attorney, Agent, or Firm*—Martin B. Barancik; Roman Saliwanchik

[57] ABSTRACT

A method of improving the endogenous production of prostaglandins by a mammal is disclosed, which comprises administering to the mammal an effective amount of certain 1-pyridylalkyl-3-phenylureas. Disclosed also are novel substituted 1-pyridylalkyl-3-phenylureas and therapeutic compositions thereof which are useful in carrying out the method of the invention.

Disclosed also are methods of treating mammals for clinical conditions responsive to prostaglandins, such as, for example, male infertility, epidermal injuries, atonic uterine bleeding, thromboembolic disease and like clinical conditions.

11 Claims, No Drawings

PYRIDYLALKYL PHENYL UREAS AND THEIR N-OXIDES

CROSS REFERENCE TO RELATED APPLICATIONS

This application is a continuation-in-part application of our co-pending application Ser. No. 428,361, filed Dec. 26, 1973 and now abandoned.

BACKGROUND OF THE INVENTION

1. Field of the Invention

The invention is concerned with the production of endogenous prostaglandins by mammals and more specifically concerns a method of raising prostaglandin production levels in the mammal by administering 1-pyridylalkyl-3-phenylureas. The invention also concerns a novel group of substituted 1-pyridylalkyl-3-phenylureas and therapeutic compositions thereof.

2. Description of the Prior Art

Natural prostaglandins are a well-known group of physiologically active unsaturated hydroxy-substituted fatty acids which are biosynthesized endogenously by mammals such as, for example, canines, bovines, equines, swine, and humans. Identified roles of the natural prostaglandins in mammalian physiology are illustrated by their action as mediators in the inflammatory process, as tonal agents in effecting the contractility of smooth muscle and as activators in a wide variety of mammalian reproductive processes.

Structurally, the natural prostaglandins have been arbitrarily classified into four basic families termed "PGE", "PGF", "PGA", and "PGB", respectively. The various families are composed of differing analogs and stereoisomers having as a hypothetical parent structure, prostanoic acid. For example, the principal members of the PGE family are $11\alpha,15$-hydroxy-9-keto-prosta-13-enoic acid (referred to alternatively for convenience as "$PGE_1$"); $11\alpha,15$-dihydroxy-9-keto-prosta-5,13-dienoic acid (hereinafter referred to alternatively as "$PGE_2$"); and $11\alpha,15$-dihydroxy-9-keto-prosta-5,13,17-trienoic acid (referred to alternatively for convenience as "$PGE_3$"). The principal members of the PGF family are $9\alpha,11\alpha,15$-trihydroxy-prosta 13 enoic acid (referred to alternatively for convenience as "$PGF_1\alpha$"); $9\beta,11\alpha,15$-trihydroxy-prosta-13-enoic acid (referred to alternatively for convenience as "$PGF_1\beta$"); $9\alpha,11\alpha,15$-trihydroxy-prosta-5,13-dienoic acid (hereinafter referred to alternatively for convenience as "$PGF_2\alpha$"); $9\beta,11\alpha,15$-trihydroxy-prosta-5,13-dienoic acid (referred to alternatively as "$PGF_2\beta$"); and $9\alpha,11\alpha,15$-trihydroxy prosta-5,13,17-trienoic acid (referred to alternatively as "$PGF_3\alpha$").

Physiological activity of specific natural prostaglandin compounds may be the same, different in degree or differ from the physiologic activity of other specific natural prostaglandins. It appears, however, that they all share a common property in not being continually produced and released by the mammalian tissues of origin. Instead, the prostaglandins appear to be spontaneously synthesized in situ (biosynthesis being equivalent to release) in response to certain stimuli or "trigger" mechanisms. The prostaglandins generally exhibit an extremely short biological half-life and current knowledge indicates that there is no storage of prostaglandins by body tissues or fluids, with the possible exception of seminal fluids. It has been suggested that the trigger or stimulus for endogenous prostaglandin synthesis is associated with trauma of cellular membranes. Such trauma may occur through physical or chemical activity. For example, in the normal mammal carrying a fetus, circulating blood and amniotic fluids do not contain significant amounts of the prostaglandins $PGE_2$ and $PGF_2\alpha$ until birth is imminent. At that time the levels of $PGE_2$ and $PGF_2\alpha$ produced by placental and uterine tissues rise substantially. The suggested function of the prostaglandins at this stage of pregnancy is to stimulate uterine contractions, i.e., labor induction. As another example, injury to mammalian epidermal tissue triggers the in situ synthesis of $PGE_2$ at the site of injury. $PGE_2$ is known to promote and accelerate healing of epidermal wounds (see, for example, U.S. Pat. No. 3,711,515 at Column 5, lines 1–11).

We have discovered that the quantity of prostaglandins produced endogenously by a mammal following the stimulation of biosynthesis will be greatly enhanced, e.g., by from 5 to 10 percent to several times normal production, when certain 1-pyridylalkyl-3-phenylureas have been systemically administered to the mammal prior to the stimulation of biosynthesis by normal trigger mechanisms.

Prior to our invention there was a suggestion that thrombin caused an increase in the production levels of $PGE_2$ and $PGF_2\alpha$ by mammalian blood platelets (Smith et al., Nature New Biol. 231–235).

Prior to our invention the treatment of clinical conditions responsive to the presence of prostaglandins had been limited to the administration of prostaglandins from exogenous sources. The method of our invention has a number of advantages over the administration of exogenous prostaglandins. For example, as mentioned above, the biological half-life of the naturally occurring prostaglandins is extremely short. Illustratively, it has been reported that after about 20 minutes, 500 µg. of $PGF_2\alpha$ administered intravenously to an adult human cannot be detected in the body. Therefore, to treat clinical conditions such as an epidermal injury with exogenous sources of prostaglandins, it is necessary to employ a continuous administration of the desired prostaglandin over a prolonged period of time. By our method, therapeutic levels of the desired prostaglandin are delivered at the "target site" or site of injury with maximum efficiency. Sustained high levels of prostaglandin are observed for several hours following treatment according to our method thus eliminating the need for continuous exogenous prostaglandin administration over long periods of time. In addition, the systemic administration of exogenous prostaglandins delivers the prostaglandin to organs and tissues other than those at the desired target site. This may result in undesirable responses or "side effects". By the method of our invention, therapeutic levels of natural prostaglandins are produced at the target site, i.e., at the point of epidermal injury or at the locality stimulating synthesis. This reduces the likelihood of responses in remotely located tissues, minimizing side-effects.

Prior hereto, a number of 1-pyridylalkyl and 1-alkyl-pyridylalkyl-3-phenylureas were known. See, for example, U.S. Pat. Nos. 3,128,280; 3,700,678; Skinner, et al., J. Org. Chem. 25, 2046, (1960); Scully et al., J. Am. Chem. Soc., 75, 3400, (1973); Robison et al., J. Am. Chem. Soc., 77, 6554, (1955); Shibanov et al., U.S.S.R., 194, 825, (1967); Novikov et al., 2h. Prikl. Khim., 42, 2373 (1969; Juby et al., J. Med. Chem., 10, 491, (1967); and Novikov, Khim. Geterotsikl. Soedin., (1), 115–116, (1968).

SUMMARY OF THE INVENTION

The invention comprises a method of increasing the production of endogenous prostaglandins by a mammal which comprises administering to said mammal an effective amount of a compound selected from those of formula:

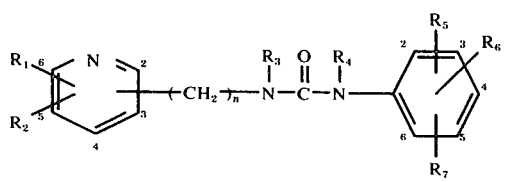

pyridyl N-oxides thereof and pharmaceutically acceptable acid addition salts thereof wherein $R_1$ and $R_2$ are each selected from hydrogen, halogen, hydrocarbyl having 1–6 carbon atoms, inclusive, alkoxy, alkylthio, nitro, amino, alkylamino, dialkylamino, acylamino and trihalomethyl; $R_3$ and $R_4$ are each selected from hydrogen, lower alkyl, alkenyl, cycloalkyl, aryl, aralkyl and aryl substituted with a group selected from halogen, lower alkoxy, and nitro; $R_5$ is selected from hydrogen, halogen, hydrocarbyl, alkoxy and halogen-substituted hydrocarbyl with one to three halogen atoms; $R_6$ and $R_7$ are each selected from nitro, cyano, amino, acylamino, alkylamino, dialkylamino, alkylthio, arylthio, aryloxy and a group $R_5$ as previously defined; and $n$ is an integer of from 1 to 2, inclusive; provided that when one of $R_5$, $R_6$ and $R_7$ is chlorine, the pyridine ring moiety of the compound (I) is attached to the rest of the molecule through the pyridyl ring carbon atom at the 4-carbon position.

Preferred for carrying out the method of the invention are those compounds (I) having the more specific formula:

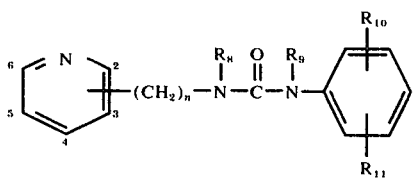

together with the pyridyl N-oxides thereof and the pharmaceutically acceptable acid addition salts thereof wherein $n$ is as previously defined; $R_8$ and $R_9$ are each selected from hydrogen, lower alkyl and phenyl; $R_{10}$ and $R_{11}$ are each selected from hydrogen, halogen, lower alkyl, lower alkoxy, trihalomethyl and nitro provided that when one of $R_{10}$ and $R_{11}$ is chlorine, the pyridine moiety of the compound of Formula (II) is attached to the rest of the molecule through the pyridyl ring carbon atom at the 4-carbon position. Of the compounds (II), those having the more specific formula:

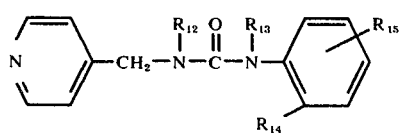

pyridyl N-oxides thereof and the pharmaceutically acceptable acid addition salts thereof wherein $R_{12}$ and $R_{13}$ each represent hydrogen or lower alkyl; $R_{14}$ and $R_{15}$ are each selected from hydrogen, halogen, lower alkyl, lower alkoxy and trifluoromethyl are particularly preferred for carrying out the method of the invention.

The invention also comprises novel compounds within the scope of Formula (I) and having the Formula (I) provided that when $R_1$ and $R_2$ are both selected from hydrogen and alkyl, said novel compound is selected from those wherein $R_7$ is selected from cycloalkyl, aryl, aralkyl, alkenyl, cyano, amino, acylamino, alkylamino, dialkylamino, alkylthio, arylthio and those wherein $R_4$ is selected from cycloalkyl, aralkyl, aryl, and aryl substituted with a group selected from halogen, lower alkoxy, lower alkyl, nitro; and the pharmaceutically acceptable acid addition salts thereof.

Preferred among the novel compounds of the invention for use in the method of the invention are those of the more specific formula:

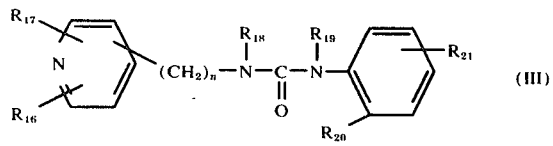

the pyridyl N-oxides thereof and the pharmaceutically acceptable acid addition salts thereof wherein $n$ is as previously defined; $R_{16}$ and $R_{17}$ are each selected from hydrogen and hydrocarbyl having 1 to 6 carbon atoms, inclusive; $R_{18}$ and $R_{19}$ are each selected from hydrogen, lower alkyl, lower cycloalkyl, and phenyl; $R_{20}$ is selected from cyano, alkoxy and alkylthio, and $R_{21}$ is selected from hydrogen, hydrocarbyl of one to six carbon atoms, halogen, nitro, alkoxy, alkylthio and halogen-substituted lower alkyl; provided that when $R_{21}$ is chlorine, the pyridine ring moiety of the compound (III) is attached to the rest of the molecule through the pyridyl ring carbon atom at the 4-carbon position.

The term "halogen" is used herein in its conventional sense as embracive of chlorine, bromine, fluorine and iodine and the term "halo" means chloro, bromo, fluoro and iodo respectively.

The term "hydrocarbyl" is used throughout the specification and claims as meaning the monovalent moiety obtained by removal of a hydrogen atom from a parent hydrocarbon, which contains 1 to 12 carbon atoms. Illustrative of such moieties are alkyl of 1 to 12 carbon atoms, inclusive, such as methyl, ethyl, propyl, butyl, pentyl, hexyl, heptyl, octyl, nonyl, decyl, undecyl, dodecyl and isomeric forms thereof; cycloalkyl of 3 to 8 carbon atoms, inclusive, such as cyclopropyl, cyclobutyl, cyclopentyl, cyclohexyl, cycloheptyl, cyclooctyl and the like; alkenyl of 2 to 12 carbon atoms, inclusive; such as vinyl, allyl, butenyl, pentenyl, hexenyl, heptenyl, octenyl, nonenyl, decenyl, undecenyl, dodecenyl and isomeric forms thereof; aryl of 6 to 12 carbon atoms, inclusive, such as phenyl, tolyl, xylyl, naphthyl, biphenylyl and the like, aralkyl of 7 to 12 carbon atoms, inclusive, such as benzyl, phenethyl, phenpropyl, phenbutyl, phenpentyl, phenhexyl and the like. When used in this specification and claims, the term "alkyl" "cycloalkyl", "alkenyl", "aryl" and "aralkyl" have the meanings employed here.

The term "halogen-substituted hydrocarbyl" means hydrocarbyl as defined above wherein one or more hydrogen atoms have been replaced with a halogen atom as defined above. Illustrative of halogen-substituted hydrocarbyl are trichloromethyl, bromocyclobutyl, 1,2-diiodovinyl, chlorophenyl, p-chlorobenzyl and the like.

The term "alkoxy" is used herein to mean the monovalent moiety of the formula:-

— O — alkyl wherein alkyl is as described above. Illustrative of alkoxy are methoxy, ethoxy, butoxy, pentyloxy, heptyloxy, decyloxy, dodecyloxy and the like.

The term "alkylthio" means the monovalent moiety of formula:-

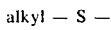
alkyl — S — wherein alkyl is as defined above. Representative of alkylthio are methylthio, pentylthio, dodecylthio and the like.

The term "aryloxy" as used herein means the monovalent moiety of formula:-

aryl — O — wherein aryl is as before defined. Illustrative of aryloxy are phenoxy, naphthoxy, and the like.

The term "arylthio" is used herein to mean the monovalent moiety of formula:-

aryl — S — wherein aryl is as defined above. Illustrative of arylthio are phenylthio, naphththio, and the like.

The term "alkylamino" is used herein to mean an amino group wherein one hydrogen atom has been replaced with an alkyl group as previously defined. Illustrative of alkylamino are methylamino, butylamino, dodecylamino, and the like.

The term "dialkylamino" is used to mean an amino group wherein both hydrogen atoms have been replaced with alkyl groups as defined above. Illustrative of dialkylamino are groups such as dimethylamino, ethylhexylamino, didodecylamino and the like.

The term "acylamino" as used herein means the monovalent moiety of formula:-

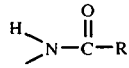

wherein R is alkyl as previously defined.

The term "lower alkyl" means alkyl as previously described having 1 to 4 carbon atoms, inclusive, and the term "lower alkoxy" means alkoxy as defined above having 1 to 4 carbon atoms, inclusive.

One skilled in the art will appreciate a variety of useful procedures which may be carried out by using the method of our invention. For example, natural prostaglandins are sought after for biological studies and as therapeutics in the treatment of mammals for a variety of clinical conditions. The extraction and recovery of natural prostaglandins from animal tissues such as lung tissue, male accessory genital glands and the like obtained from sacrificed animals is a costly procedure and any improvement of yields is a significant commercial factor. By the method of our invention, effective amounts of compounds of the formula (I) its pyridyl N-oxides and its pharmaceutically acceptable acid addition salts thereof are administered to the natural prostaglandin-producing animal within a period of from 1 to 6 hours prior to sacrifice. This results in enhanced yields of prostaglandins recovered by conventional and known methods of extraction.

By the method of our invention, mammal treatment procedures for a variety of clinical conditions responsive to prostaglandins are improved. More specifically, those clinical conditions which are related to a prostaglandin deficiency or which respond to enhanced levels of prostaglandins and in which there is an operative trigger mechanism for stimulation of prostaglandin production are advantageously responsive to the method of our invention. Illustratively, some 13 different prostaglandins, representing all four prostaglandin families are found in mammalian seminal fluids. A correlation exists between low prostaglandin levels (particularly of the PGE family) in seminal fluids and male infertility; see, for example, "The Prostaglandins", Karim, Medical and Technical Pub. Co. Ltd., Oxford (1972) pp. 134–6. In those instances wherein seminal fluid prostaglandins are produced by the mammal, but in low quantity, production levels are raised by the method of our invention. Thus, the method of our invention provides a method of treating mammalian male infertility which comprises administering to said male an effective amount of a compound (I) or a pyridyl N-oxide or a pharmaceutically acceptable acid addition salt thereof.

To further illustrate the use of the method of our invention, it is known that the prostaglandin $PGE_2$ is produced at the site of epidermal injury in a mammal [see for example Anggard et al., Alza Conference on Prostaglandins in Cellular Biology, Edited by Ramwell and Pharriss, Plenum Press, N.Y., N.Y. (1972), page 269.] The generally accepted role of $PGE_2$ at the site of injury following, for example, burns, abrasions, surgery, penetration wounds and like epidermal injuries is to stimulate epidermal cell proliferation and keratin formation, thereby accelerating wound healing. It should be further noted that the term "epidermal injury" is broad enough in this context to include skin conditions such as psoriasis wherein the $PGE_2$ stimulates production of cyclic AMP which additionally aids in overcoming the effects of the condition. By using the method of our invention, higher levels of $PGE_2$ are obtained over long periods of time to accelerate the healing process. Thus, a preferred embodiment of the method of our invention comprises a method of promoting the healing of epidermal injuries in a mammal which comprises administering to said mammal an effective amount of a compound selected from those of the formula (I), pyridyl N-oxides thereof and pharmaceutically acceptable acid addition salts thereof. Surprisingly, although $PGE_2$ is a known mediary in the inflammatory process, the method of our invention so employed does not produce a significant increase in the manifestations generally associated with inflammation such as pain, edema, swelling and like inflammatory manifestations.

In another use, the method of our invention is employed advantageously to prevent or control atonic uterine bleeding. $PGE_2$ and $PGF_2\alpha$ are both produced by the endometrium and blood platelets (upon aggregation). In situations of post-partum hemorrhage due to an atonal uterus, the elevation of $PGE_2$ and $PGF_2\alpha$ production by platelets at the site of bleeding provides therapeutic levels of the two prostaglandins sufficient to render tone to the uterine muscle, thus causing sustained contractions of the uterus and controlling hemorrhage. The method of our invention therefore includes as an embodiment the prevention and control of atonic uterine hemorrhage in a mammal which comprises administering to the mammal an effective amount of a compound selected from those of formula (I), pyridyl N-oxides thereof and pharmaceutically acceptable acid addition salts thereof. Administration of the compound (I), its N-oxides or its salts in this particular use is advantageously carried out during a period of from 1 to 6 hours before an anticipated hemorrhage to prevent the same, or immediately following the start of hemorrhage. In the latter instance, control of bleeding generally occurs within from 1 to about 3 hours of administration.

As mentioned above, $PGF_2\alpha$ and $PGE_2$ are both produced by the mammalian blood platelet upon stimulation of synthesis by cell aggregation. Build-up of $PGF_2\alpha$ and $PGE_2$ levels at the site of platelet aggregation are associated with inhibition of further platelet aggregation, thereby terminating the continued development of thrombi. By the method of our invention, one may terminate the development of thrombi earlier and more rapidly through enhanced levels of $PGF_2\alpha$ and $PGE_2$ production. This is particularly useful in the treatment and prevention of myocardial infarcts, post-operative thrombosis, atherosclerosis, arteriosclerosis and like clinical conditions where the development of a thrombus is undesired. Thus, another embodiment of our invention comprises a method of controlling the development of a thrombus in a mammal which comprises administering an effective amount of a compound selected from those of formula (I), pyridyl N-oxides thereof and pharmaceutically acceptable acid addition salts thereof, to said mammal.

DETAILED DESCRIPTION OF THE INVENTION

The compounds (I), pyridyl N-oxides thereof and pharmaceutically acceptable acid addition salts thereof are administered to the mammal systemically and topically. Illustrative of methods of administration are oral, parenteral and topical administrations. Oral and parenteral administrations are preferred.

The effective amount administered is that quantity which brings about an increase in the production levels of prostaglandins biosynthesized by the subject mammal. The exact amount to be administered will depend upon a number of factors such as, for example, the specific compound (I), its N-oxide or salt, species of mammal, age, weight and physical condition of the mammal, route of administration and in the instances wherein a specific clinical condition is being treated by the method of the invention, the nature of the condition. In general, prostaglandin production levels rise in direct proportion to the quantity of the compound (I), its N-oxide or acid addition salt administered.

The exact dosage requirement in a given clinical situation may be determined by administration of a trial dose and observation of the prostaglandin production response by blood plasma analysis or by clinical response to the presence of prostaglandin. In general, an effective amount to be administered is within the range of from about 0.1 mg. to about 500 mg. per kilogram of body weight of the recipient mammal and preferably within the range of from about 5 mg. to about 50 mg. per kilogram body weight. In general, the degree of response is related to dose, and higher doses produce faster and more complete clinical responses. In most instances, a single administration will effect the desired response and bring about the result desired. In cases such as in the treatment of epidermal injuries, however, it may be desirable to repeat the administrations several times. In such instances, we have noted a decrease in degree of prostaglandin production response upon administrations subsequent to the first administration unless there is a resting period between administrations. Resting periods of from about 12 to about 24 hours between administrations assure the highest prostaglandin production for a given dosage of the compounds (I), their N-oxides and pharmaceutically acceptable acid addition salts.

Although all mammalian tissues capable of producing prostaglandins are responsive to the method of our invention, the most advantageous response is obtained from circulating blood platelets which produce $PGE_2$ and $PGF_2\alpha$. The platelets produce larger quantities of these prostaglandins and serve to meet therapeutic needs as described above most readily and conveniently. The method of our invention is particularly advantageous in stimulating high yields of $PGF_2\alpha$ from the producing blood platelets.

Illustrative of the known compounds of formula (I) employed in the method of our invention are 1-(2-pyridylmethyl)-3-phenylurea, 1-(3-pyridylmethyl)-3-phenylurea and 1-(4-pyridylmethyl)-3-phenylurea [see Skinner et al., J. Org. Chem. 25, 2046-7 (1960)]; 1-(2-pyridylethyl)-3-phenylurea; 1-(4-pyridylethyl)-3-phenylurea, 1-(2-pyridylethyl)-3-(4-methoxyphenyl)urea and 1-(4-pyridylethyl)-3-(4-methoxyphenyl)urea [see Sheob et al., Indian J. Chem., 5, 145 (1967)]; 1-[2-methylpyridyl(methyl)]-3-phenylurea, 1-[2-methylpyridyl(methyl)]-3-(2-chlorophenyl)urea, 1-[2-methylpyridyl(methyl)]-3-(3-chlorophenyl)urea, 1-[2-methylpyridyl(methyl)]-3-(4-chlorophenyl)urea and 1-[2-methylpyridyl(methyl)]-3-(2,5-dichlorophenyl)urea [see Juby et al., J. Med. Chem., 10, 491 (1967)]; 1-methyl-1-(2-pyridylmethyl)-3-phenylurea, 1-methyl-1-(2-pyridylmethyl)-3-(4-methylphenyl)urea, 1-methyl-1-(2-pyridylmethyl)-3-(3-chlorophenyl)urea, 1-methyl-1-(2-pyridylmethyl)-3-(3,4-dichlorophenyl)urea, 1-methyl-1(2-pyridylmethyl)-3-(3-nitrophenyl)urea, 1-methyl-1-(2-pyridylmethyl)-3-(3-trifluoromethylphenyl)urea, 1-methyl-1-(2-pyridylmethyl)-3-(4-chloro-3-trifluoromethylphenyl)-urea, 1-methyl-1-(2-pyridylmethyl)-3-(4-chlorophenyl)urea, 1-methyl-1-(2-pyridylmethyl)-3-(3-fluorophenyl)urea, 1-methyl-1-(2-pyridylmethyl)-3-(4-chloro-3-nitrophenyl)urea, 1-methyl-1-(2-pyridylmethyl)-3-(3,4-dichlorophenyl)urea, 1-methyl-1-(3-pyridylmethyl)-3-(4-chloro-3-fluorophenyl)-urea, 1-methyl-1-(3-pyridylmethyl)-3-(4-chloro-3-nitrophenyl)urea, 1-methyl-1-(3-pydridylmethyl)-3-(4-methylphenyl)urea, 1-methyl-1-(3-pyridylmethyl)-3-(3,4-dimethylphenyl)urea, 1-methyl-1-(4-pyridylmethyl)-3-(3,4-dichlorophenyl)urea, 1-methyl-1-(4-pyridylmethyl)-3-(3-fluorophenyl)urea, 1-methyl-1-(4-pyridylmethyl)-3-(4-methylphenyl)urea, 1-methyl-1-(4-pyridylmethyl)-3-(3-nitrophenyl)urea, and 1-methyl-1-(4-pyridylmethyl-3-(3-trifluoromethylphenyl)urea (see U.S. Pat. No. 3,700,678); 1-(2-chlorophenyl)-3-($\alpha$-phenyl-4-pyridylmethyl)urea, 1-methyl-1-(4-pyridylmethyl)-3-(4-bromophenyl)urea, 1-methyl-1-(4-pyridylmethyl)-3-

(4-iodophenyl)urea, 1-butyl-1-(4-pyridylmethyl)-3-methyl-3-(2-chlorophenyl)urea, 1-(4-pyridylmethyl)-3-(3,4,5-trimethoxyphenyl)urea, 1-(2-pyridylmethyl)-3-(3,4,5-trimethoxyphenyl)urea, 1-(4-methoxyphenyl)-3-(α-phenyl-4-pyridylmethyl)urea, 1-(3,4,5-trimethoxyphenyl)-3-(α-phenyl-4-pyridylmethyl)-urea, 1-methyl-1-(4-pyridylmethyl)-3-(4-methoxyphenyl)-urea, 1-methyl-1-(4-pyridylmethyl)-3-(4-ethoxyphenyl)-urea, 1-methyl-1-(4-pyridylmethyl)-3-(2-ethoxyphenyl)-urea, 1-methyl-1-(3-pyridylmethyl)-3-(4-ethoxyphenyl)-urea, and 1-methyl-1-(2-pyridylmethyl)-3-(4-ethoxyphenyl)-urea (see U.S. Pat. No. 3,128,280).

The compounds (I) wherein $R_4$ is specifically hydrogen and $R_6$ and $R_7$ are other than amino, alkylamino or acylamino; i.e., a compound of the formula (VI); are readily prepared by the method set forth in U.S. Pat. No. 3,128,280. In general, the method comprises reacting an appropriate aminoalkylpyridine (IV) with an appropriate phenylisocyanate (V). The reaction is conveniently illustrated by the schematic formula:

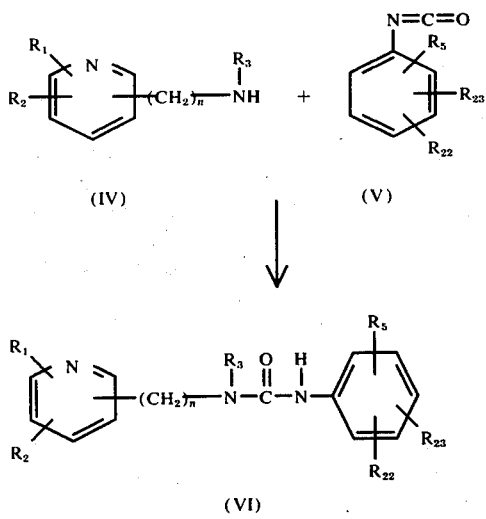

wherein $n$, $R_1$, $R_2$, $R_3$ and $R_5$ are as defined above; $R_{22}$ and $R_{23}$ are each selected from nitro, cyano, dialkylamino, alkylthio, arylthio, aryloxy and a group $R_5$ as defined previously.

The above illustrated reaction proceeds satisfactorily by adding the isocyanate reactant (V) to a solution of the aminoalkylpyridine (IV) in an inert organic solvent. An inert organic solvent is a solvent for reactant (IV) which does not react with components of the reaction mixture, or in any way interfere with the desired course of the reaction. Illustrative of inert organic solvents are tetrahydrofuran, dioxane, benzene, pyridine and the like. Generally, the above reaction is carried out at a temperature of from about 0° C. to 100° C. and is complete within 1 to 48 hours depending upon the nature of substituents $R_1$, $R_2$, $R_3$, $R_5$, $R_{22}$ and $R_{23}$. Completion of the reaction may be observed by conventional analytical techniques such as by infrared spectral analysis and thin-layer chromatography which will indicate the disappearance of the isocyanate reactant. Upon completion of the reaction, the desired product compounds (IV) are readily separated from the reaction mixture by conventional methods such as, for example, by distillation, crystallization, and like methods. For complete details of the above described method, see U.S. Pat. Nos. 3,128,280 and 3,700,678.

The starting aminoalkylpyridine compounds (IV) employed in the above described reaction are generally well known, and may be prepared by a variety of methods, see for example, Scully et al., supra., Shuman et al., J. Org. Chem., 27, 1970 (1962); Bobbitt et al., J. Org. Chem., 29, 2298 (1964); Bower et al., J. Chem. Soc., 2834 (1955); Bruce et al., J. Am. Chem. Soc., 66, 2092 (1944); and Sam, J. Pharm. Sci., 56, 1202 (1967).

A convenient method of preparing the aminoalkylpyridines (IV) wherein $R_1$ and $R_2$ are other than acylamino groups is by reduction of the corresponding amide compounds of formula:

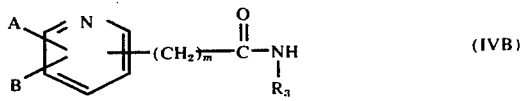

wherein $m$ is an integer of from 0 to 1 and $R_3$ is as defined above; A and B are each selected from hydrogen, halogen, hydrocarbyl of 1 to 6 carbons, inclusive, alkoxy, alkylthio, nitro, amino, alkylamino, dialkylamino, and trihalomethyl. The methods of reduction are well known, see for example, Tarbell et al., J. Am. Chem. Soc., 72, 2657 (1950); Uffer et al., Helv. Chim. Acta., 31, 1397 (1948); and Brown, Org. Reactions, Vol. 6, J. Wiley and Sons, N.Y., N.Y., (1951), page 469.

The amides of formula (IVB) may be prepared by the method of Zymalkowski et al., Arch. Pharm. 293, 47–53 (1960) which comprises heating the corresponding pyridyl acetate with an appropriate amine. Representative of the compounds (IVB) are 2-chloro-6-ethylthioisonicotinamide, N-butyl-2-ethylthioisonicotinamide, N-butyl-2,6-dichloroisonicotinamide, N-benzyl-4-pyridylacetamide, 2-chloro-6-methoxy-N-(α-methyl phenylethyl)isonicotinamide, 2-pyridineacetanilide, N-cyclopropylisonicotinamide, 2,6-dichloro-N-(cyclopropylmethyl)isonicotinamide, 4'-phenoxynicotinanilide, 2'-phenylnicotinanilide, N-butyl-6-methylthiopicolinamide, N-cyclohexylpicolinamide, 5'-methyl-4'-nitro-o-picolinanisidide, 4'-cyclohexylnicotinanilide, 4,6-dichloropicolinamide, 4-ethoxypicolinamide, 5-ethylthiopicolinamide, N-1-naphthylisonicotinamide, 4'-chloroisonicotinanilide, p-isonicotinanisidine, 2'-chloro-4'-nitropicolinanilide, 2',5'-diethoxy-4'-nitropicolinanilide and the like.

An alternative method of preparing the aminoalkylpyridines (IV) wherein $R_3$ is specifically hydrogen and the method for preparing compounds (IV) wherein $R_1$ or $R_2$ is an acylamino group is that disclosed by Scully et al., supra., which comprises reducing the corresponding nitrile compounds of formula:

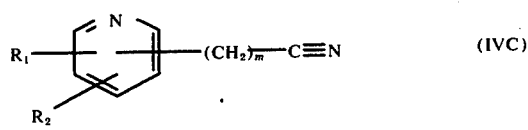

wherein $R_1$, $R_2$ and $m$ are as before defined. Representative of the compounds (IVC) are picolinonitrile, 4-chloropicolinonitrile, 4,6-dimethylpicolinonitrile, 4-phenylpicolinonitrile, 4-benzylpicolinonitrile, 3-allylpicolinonitrile, 4-methoxypicolinonitrile, 2,5-diethoxypicolinonitrile, 4-methylthiopicolinonitrile, 3,5-dinitropicolinonitrile, 3,5-diaminopicolinonitrile, 3-ethylaminopicolinonitrile, 3-diethylaminopicolinonitrile, 4-acetylaminopicolinonitrile, 4-trifluoromethylpiconitrile and the like.

Those compounds (IV) wherein $R_3$ is as defined previously but other than hydrogen and $R_1$ or $R_2$ are acylamino are prepared by N-acylating the corresponding compound (IV) wherein the appropriate group $R_1$ or $R_2$ is an amino group. The method of N-acylation may be conventional such as, for example, by reaction with an appropriate alkyl carboxylic acid, such as acetic acid, heptanoic acid, dineopentylacetic acid and the like.

The starting isocyanate compounds (V) employed in preparing the compounds (I) are generally well known in the art as is their preparation by phosgenation of the corresponding primary amine. Illustrative of the compund (V) are phenylisocyanate, p-chlorophenylisocyanate, o-fluorophenylisocyanate, p-bromophenylisocyanate, 3,4-dichlorophenylisocyanate, 4-bromo-2-chlorophenylisocyanate, 4-iodophenylisocyanate, 2,4,5-tribromophenylisocyanate, 4-bromo-3-fluorophenylisocyanate, o-methylphenylisocyanate, p-dodecylphenylisocyanate, 2,4-dimethylphenylisocyanate, 4-tert-butyl-2,6-diethylphenylisocyanate, 2,4-ditert-butylphenylisocyanate, 2,6-diethylphenylisocyanate, p-cyclohexylphenylisocyanate, 3-chloro-2-methylphenylisocyanate, 2-phenylphenylisocyanate, m-methoxyphenylisocyanate, p-ethoxyphenylisocyanate, 3,4-dimethoxyphenylisocyanate, 4-butoxyphenylisocyanate, 5-chloro-2-methoxyphenylisocyanate, 2-methoxy-5-methylphenylisocyanate, p-trifluoromethylphenylisocyanate, p-chlorophenylphenylisocyanate, m-nitrophenylisocyanate, 3,5-dinitrophenylisocyanate, 3-nitro-o-tolylisocyanate, 2-methoxy-4-nitrophenylisocyanate, 2-bromo-4-nitrophenylisocyanate, 2,6-dichloro-4-nitrophenylisocyanate, p-cyanophenylisocyanate, 3-chloro-4-cyanophenylisocyanate, o-phenoxyphenylisocyanate, 3-chloro-4-(methylthio)phenylisocyanate, 3-chloro-4-(ethylthio)phenylisocyanate, o-(phenylthio)phenylisocyanate, p-(diethylamino)phenylisocyanate and the like.

The compounds (I) wherein $R_3$ is specifically hydrogen and $R_1$ and $R_2$ are as previously defined but other than amino, alkylamino or acylamino; i.e., compounds of formula (VII) are also prepared by the same general method described in U.S. Pat. Nos. 3,128,280 and 3,700,678 employing as the reactants, however, a pyridylalkylisocyanate (VIII) and an aniline (IX). The reaction is illustrated schematically by the formula:

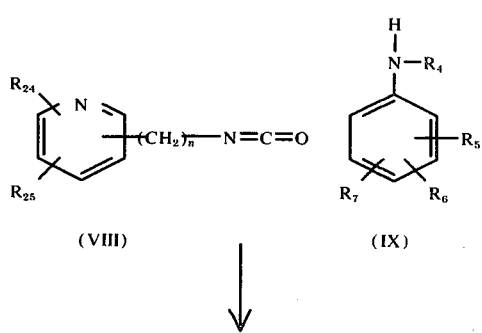

(VIII)    (IX)

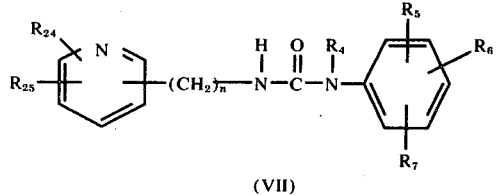

(VII)

wherein $n$, $R_4$, $R_5$, $R_6$ and $R_7$ are as previously defined; $R_{24}$ and $R_{25}$ are each selected from hydrogen, halogen, hydrocarbyl of 1 to 6 carbons, inclusive, alkoxy, alkylthio, nitro, dialkylamino and trihalomethyl.

Pyridylalkylisocyanates of formula (VIII) are prepared by phosgenation of the corresponding primary pyridylalkylamine such as those within the scope of formula (IV) previously described. The techniques of phosgenating primary amines to prepare corresponding isocyanates are well known, see for example Polyurethanes Chemistry and Technology; Part I, Saunders and Frisch, Interscience, N.Y., N.Y. (1962), pp. 18–29. Starting aniline compounds (IX) used in the above described reaction are generally well known and are represented by aniline, p-chloroaniline, 2,5-dibromoaniline, 3,4,5-trichloroaniline, m-toluidine, 3,5-dibutylaniline, 3-allylaniline, p-phenylaniline, p-benzanilide, m-phenetidine, 3,4,5-trimethoxyaniline, m-dichloromethylaniline, p-(p-chlorophenyl)aniline, p-nitroaniline, m-cyanoanilide, p-phenylenediamine, p-acetylaminoaniline, o-methylaminoaniline, o-dimethylaminoaniline, 2,5-dimethylthioaniline, p-phenylthioaniline, p-phenoxyaniline, o-(2-chloroethyl)aniline, 4-methylthio)aniline, 3-(ethylthio)-4-(methylthio)aniline, 4-bromo-2-chloroaniline, 2-bromo-4,6-dinitroaniline, 2-bromo-4-methylaniline, 2-bromo-4-nitroaniline, 3-chloro-o-anisidine, 5-chloro-2,4-dimethoxyaniline, 4-fluoro-3-nitroaniline, p-(2,2,2-trichloroethyl)aniline, N-methyl-aniline, N-butyl-aniline; N-cyclohexyl-aniline, N-phenyl-aniline, N-benzyl-aniline, N-(p-nitrophenyl)-aniline, N-(o-methylphenyl)-aniline, N-biphenyl-aniline, N-(p-phenoxy-phenyl)-aniline and the like.

Those compounds (I) wherein $R_1$, $R_2$, $R_6$ and $R_7$ are specifically selected from amino, alkylamino, and acylamino are prepared from the corresponding compounds (I) wherein $R_6$ and/or $R_7$ are nitro groups. Thus, by conventional methods of reduction [see for example the method of Pietra, Ann. Chim., 45, 850 (1955)] the nitro substituent group is reduced to an amino group; and by conventional methods well known in the art, such as by reaction with an appropriate alkyl halide of formula:

alkyl—X wherein X represents halogen the primary amino groups may be converted to alkylamino groups [see for example the method of Johnstone et al., J. Chem. Soc., (C), 2223 (1969)]. When desired, conversion of the $R_1$, $R_2$, $R_6$ and/or $R_7$ substituent amino groups to an acylamino group is also carried out by conventional and known methods, such as by reaction of said amino group with an appropriate acid anhydride or acyl halide of the formula:

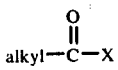

where X and alkyl are as defined previously.

An alternate method of preparing the compounds (I) is also described in U.S. Pat. 3,128,280. In general, the alternate method comprises reacting an aminoalkylpyridine (IV) as previously described with an appropriate N-phenyl carbamoyl chloride (X) according to the schematic formula:

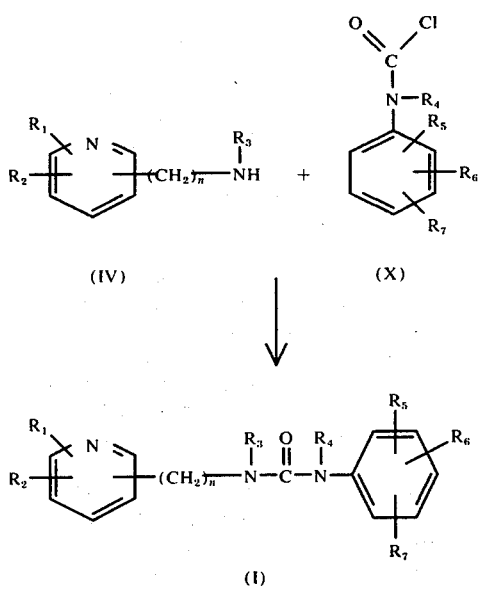

wherein $n$, $R_1$, $R_2$, $R_3$, $R_4$, $R_5$, $R_6$, and $R_7$ are as defined above.

In the above described alternate method, the starting carbamoyl reactants (X) are prepared by conventional phosgenation of the corresponding aniline (IX) supra.; see for example, the method of K. Palat et al., Chem. Listy, 51, 563 (1957) and of German Patent 870,097.

The pyridyl N-oxides of the compounds (I), i.e., compounds of the formula:-

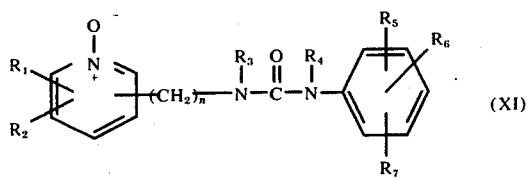

corresponding to the compounds (I) and the pharmaceutically acceptable acid addition salts thereof wherein $R_1$, $R_2$, $R_3$, $R_4$, $R_5$, $R_6$, $R_7$ and n have the meanings previously ascribed to them, are also novel compounds and are useful for the same purposes and in the same manner as the nonoxides of formula (I).

The pryidyl N-oxides (XI) are prepared by N-oxidation of the corresponding compound (I). Such oxidations are well known and are generally carried out by reacting the compound (I) with an excess molar proportion of an oxidizing agent such as hydrogen peroxide. See, for example, the procedure disclosed by E. Ochiai, Aromatic Amino Oxides, Elsevier Publishing Company, New York, p. 25 (1967).

The pharmaceutically acceptable acid addition salts of the compounds (I) and (XI) may be used for the same purposes as the corresponding free base compounds, and in the same manner. They are readily prepared by reacting the free base with a stoichoimetric proportion of an appropriate acid. The method is well known to those skilled in the art and may be carried out in aqueous or nonaqueous media such as ethanol, ether, ethyl acetate and the like. Illustrative of pharmaceutically acceptable acid addition salts are those formed upon reaction of the free base compound (I) or compound (XI) with hydrochloric acid, hydrobromic acid, sulfuric acid, phosphoric acid, acetic acid, lactic acid, citric acid, succinic acid, benzoic acid, salicylic acid, pamoic acid, cyclohexanesulfamic acid and the like.

This invention relates also to pharmaceutical dosage unit forms for systemic effects (oral, parenteral and rectal administration) and topical administration which are useful in improving the production of endogenous prostaglandins by mammals, including humans. The term "dosage unit form" as used in this specification and in the claims refers to physically discrete units suitable as unitary dosaged for mammalian subjects, each unit containing a predetermined quantity of the essential active ingredient, i.e., a compound of formula (XI); or a compound of the formula (I) wherein it is provided that when $R_1$ and $R_2$ are both selected from hydrogen and alkyl, said compound (I) is selected from those wherein $R_7$ is selected from cycloalkyl, aryl, aralkyl, alkenyl, cyano, amino, acylamino, alkylamino, dialkylamino, arylthio, alkylthio and those wherein $R_4$ is selected from cycloalkyl, aralkyl, aryl and aryl substituted with a group selected from halogen, lower alkoxy, hydrocarbyl, or one to six carbon atoms, inclusive, nitro or pharmaceutically acceptable acid addition salts thereof, calculated to produce the desired effect in combination with the required pharmaceutical means which adapt said ingredient for systemic administration. Examples of dosage unit forms in accordance with this inventon are tablets, capsules, orally administered liquid preparations in liquid vehicles, sterile preparations in liquid vehicles, sterile preparations in liquid vehicles for intramuscular and intravenous administration, rectal suppositories, sterile dry preparations for the extemporaneous preparation of sterile injectable preparations in a liquid vehicle, ointments, lotions, pastes, jellies, sprays, aerosols, and the like. Solid diluents or carriers for the solid oral pharmaceutical dosage unit forms are selected from the group consisting of lipids, carbohydrates, proteins and mineral solids, for example, starch, sucrose, kaolin, dicalcium phosphate, gelatin, acacia, corn syrup, corn starch, talc and the like. Capsules, both hard and soft, are formulated with conventional diluents and excipients, for example, edible oils, talc, calcium carbonate, calcium stearate and the like.

Liquid preparations for oral administration are prepared in water or aqueous solutions which advantageously contain suspending agents such as, for example, carboxymethylcellulose, methylcellulose, acacia, polyvinyl pyrrolidone, polyvinyl alcohol and the like. In the instance of injectable forms they must be sterile and must be fluid to the extent that easy syringeability exists. Such preparations must be stable under the conditions of manufacture and storage, and oridinarily contain, in addition to the basic solvent or suspending liquid, preservatives in the nature of bactericidal and fungicidal agents, for example parabens, chlorobutanol, benzyl alcohol, phenol, thimerosal and the like. In many cases it is preferable to include isotonic agents, for example sugars or sodium chloride. Carriers and vehicles include vegetable oils, ethanol and polyols, for example glycerol, propylene glycol, liquid polyethylene glycol and the like. Any solid preparations for subsequent extemporaneous preparation of sterile injectable preparations are sterilized, preferably by exposure to a sterilizing gas such as, for example, ethylene oxide. The aforesaid carriers, vehicles, diluents, excipients, preservatives, isotonic agents and the like constitute the pharmaceutical means which adapt the preparations for systemic administration.

For topical use, this compound can be formulated in a pharmaceutical carrier suitable for application to affected areas of the skin, eyes, ears or mucous membranes. Accordingly, the compositions of this invention include those pharmaceutical forms in which the medication is applied externally for direct contact with the surface to be treated. Conventional pharmaceutical forms for this purpose include ointments, creams, lotions, solutions, suspensions, pastes, jellies, sprays and aerosols (e.g., for oral or nasal use or on the skin), drops (e.g., for use in the eyes or ears), powders (e.g., for use on the skin) and the like. In preparing the desired topical formulations of the novel compound of this invention, various additives, diluents and adjuvants can be utilized. These illustratively include water, surfactants (e.g., polysorbate 80 and polyoxethylene sorbitan monostearate), emulsifiers (e.g., glyceryl monostearate-diethylaminoethyl alkyl amide phosphate, isopropyl myristate and cetyl alcohol), alcohols (e.g., ethanol and isopropanol), lower alkyl diols (e.g., 1,3-butanediol, 2,3-butanediol, 1,2-propanediol, 1,3-propanediol), glycols (e.g., propylene glycol, glycerol, sorbitol), ointment-type bases (e.g., spermaceti, Carbowaxes, beeswax, petrolatum, lanolin), higher fatty acids and alcohols (e.g., stearic acid, stearyl alcohol, cetyl alcohol, palmitic acid), liquid paraffin and vegetable oils (e.g., peanut oil, castor oil), preservatives such as sorbic acid, parabens, chlorocresol, benzalkonium chloride) and solid diluents (e.g., lactose, starch, bentonite, talc).

A rectal suppository can be employed to deliver the active compound where the mammal cannot be treated conveniently by means of other dosage forms, such as orally, as in the case of young children or debilitated persons. The active compound can be incorporated into any of the known suppository bases by methods known in the art. Examples of such bases include cocoa butter, polyethylene glycols (Carbowaxes), polyethylene sorbitan monostearate, and mixtures of these with other compatible materials to modify the melting point or dissolution rate. These rectal suppositories can weigh from about 1 to 2.5 Gm.

The pharmaceutical dosage unit forms are prepared in accordance with the preceding general description to provide from about 10 to about 1500 mg. of the essential active ingredient per dosage unit form with preferably 100 to 1000 mg. in the oral and parenteral forms. With regard to topical forms, the dosage is from about one to about fifteen per weight percent of the suppository.

The following examples describe the manner and process of making and using the invention, and set forth the best mode contemplated by the inventors of carrying out the invention but are not to be construed as limiting.

EXAMPLE 1

1,1-Diphenyl-3-(3-pyridylmethyl)urea

An appropriate reaction vessel is charged with 4.32 gms. (0.04 mole) of 3-aminomethylpyridine, 4.5 gms. (0.04 mole) of triethylamine and 100 ml. of tetrahydrofuran. To the resulting mixture, 9.27 gms. (0.04 mole) of diphenylcarbamoyl chloride is added with stirring. Stirring is maintained for about 24 hours. after which the mixture is diluted with water to give a total volume of 1 liter. A solid separates which is removed, washed with water and dried. Upon recrystallization of the solid from ethanol there is obtained 5.53 gms. (47 percent of theory) of 1,1-diphenyl-3-(3-pyridylmethyl)urea in the form of tan crystals, m.p. 142.7° C.

Similarly, following the above procedure, but replacing the diphenylcarbamoyl chloride as used therein with an equal molar proportion of the following compounds of the formula (X); methyl(P3-nitro-p-anisoyl)carbamoyl chloride, methyl(3-nitro-p-tolyl)-carbamoyl chloride, and methyl(p-tolyl)carbamoyl chloride, respectively, there is obtained 1-methyl-3-(3-nitro-p-anisoyl)-3-(3-pyridylmethyl)urea, 1-methyl-1-(3-nitro-p-tolyl)-3-(3-pyridylmethyl)urea, and 1-methyl-1-(p-tolyl)-3-(3-pyridylmethyl)urea, respectively, and replacing the diphenylcarbamoyl chloride as used therein with an equal molar proportion of the following compounds of the formula (X); cyclohexylphenylcarbamoyl chloride, benzylphenylcarbamoyl chloride, (p-nitrophenyl)phenylcarbamoyl chloride o-tolylphenylcarbamoyl chloride, biphenyllylphenylcarbamoyl chloride, and phenoxyphenylphenylcarbamoyl chloride, respectively, all of which may be prepared by phosgenation of the corresponding amine of formula (IX), supra., [see the methods of Slocombe et al., J.A.C.S., 72, 1888 (1950) and Raiford et al., J. Org. Chem., 5, 306 (1940)]; there is obtained 1-methyl-1-cyclohexylphenyl-3(3-pyridylmethyl)urea, 1-methyl-1-benzylphenyl-3-(3-pyridylmethyl)urea, 1-methyl-1-[(-p-nitrophenyl)phenyl]-3-(3-pyridylmethyl)urea, 1-methyl-1(o-tolylphenyl)-3-(3-pyridylmethyl)urea, 1-methyl-1-(biphenylylphenyl)-3-(3-pyridylmethyl)urea, and 1-methyl-1-[(phenoxyphenyl)phenyl]-3-(3-pyridylmethyl)urea, respectively.

EXAMPLE 2

1,1-Diphenyl-3-(4-pyridylmethyl)urea

Following the procedure of Example 1, supra., but replacing the 3-aminomethylpyridine as used therein with 5.41 gms. (0.05 mole) of 4-aminomethylpyridine, increasing the proportion of triethylamine to 5.05 gms. (0.05 mole) and increasing the proportion of diphenyl)carbamoyl chloride to 11.58 gms. (0.05 mole) there is obtained 2.60 gms. (17 percent of theory) of 1,1-diphenyl-3-(4-pyridylmethyl)urea in the form of a pale yellow powder, m.p. 174.1° C.

Similarly, following the above procedure but replacing the 4-aminomethylpyridine as used therein with an equal molar proportion of the following compounds of formula (IV):

4-aminomethyl-2-chloropyridine,
4-aminomethyl-2,5-dimethylpyridine,
4-aminomethyl-3-allylpyridine,
4-aminomethyl-3-methoxypyridine,
4-aminomethyl-3-phenylpyridine, 4-aminomethyl-3-ethylthiopyridine,
3-aminomethyl-2,5-dinitropyridine,
3-aminomethyl-2,5-diaminopyridine,
2-aminomethyl-4-methylaminopyridine,
2-aminomethyl-4-diethylaminopyridine,
2-aminomethyl-4-acetylaminopyridine, and
2-aminomethyl-4-(trifluoromethyl)pyridine,
respectively, [all of which are prepared by reduction of the appropriate compound (IVC), method of Sculley et al., supra.)], there is obtained 1,1-diphenyl-3-[4-(2-chloropyridyl)methyl]urea,
1,1-diphenyl-3-[4-(2,5-dimethylpyridyl)methyl]urea,
1,1-diphenyl-3-[4-(3-allylpyridyl)methyl]urea,
1,1-diphenyl-3-[4-(3-methoxypyridyl)methyl]urea,
1,1-diphenyl-3-[4-(3-phenylpyridyl)methyl]urea,
1,1-diphenyl-3-[4-(3-ethylthiopyridyl)methyl]urea,
1,1-diphenyl-3-[3-(2,5-dinitropyridyl)methyl]urea,
1,1-diphenyl-3-[3-(2,5-diaminopyridyl)methyl]urea,
1,1-diphenyl-3-[2-(4-methylaminopyridyl)methyl]urea,
1,1-diphenyl-3-[2-(4-diethylaminopyridyl)methyl]urea, diethylaminopyridyl)methyl]urea,
1,1-diphenyl-3-[2-(4-acetylaminopyridyl)methyl]urea,
1,1-diphenyl-3-[2-(4-trifluoromethylpyridyl)methyl]urea.

EXAMPLE 3

1,1-Diphenyl-3-(2-pyridylethyl)urea

Following the procedure of Example 1, supra., but replacing the 3-aminomethylpyridine as used therein with 3.66 gms. (0.03 mole) of 2-aminoethylpyridine, decreasing the proportion of triethylamine as used therein to 3.03 gms. (0.03 mole) and decreasing the proportion of diphenylcarbamoyl chloride as used therein to 6.95 gms. (0.03 mole) there is obtained 5.96 g. (63 percent of theory) of 1,1-diphenyl-3-(2-pyridylethyl)urea in the form of colorless crystals, m.p. 109.1° C.

EXAMPLE 4

1,1-Diphenyl-3-methyl-3-(2-pyridylethyl)urea

An appropriate reaction vessel is charged with 6.8 gms. (0.05 mole) of 2-methyl-aminoethylpyridine, 5.05 gms. (0.05 mole) of triethylamine and 100 ml. of tetrahydrofuran. To the resulting mixture, 11.58 gms. (0.05 mole) of diphenylcarbamoyl chloride is added with stirring. After stirring at room temperature for 24 hours, the mixture is diluted with water to obtain a mixture having a volume of 1 liter. The dilute mixture is distilled to yield an oil which is 1,1-diphenyl-3-methyl-3-(2-pyridylethyl)urea.

Similarly, following the above procedure but replacing the 2-methylaminoethylpyridine as used therein with an equal molar proportion of 2-($\beta$-cyclohexylaminoethyl)pyridine,
2-($\beta$-phenylaminoethyl)pyridine,
2-($\beta$-benzylaminoethyl)pyridine, and
2-[$\beta$-(p-methoxyphenylamino)ethyl]pyridine respectively, all of which may be prepared by reduction of the corresponding amide of Formula (IVB) (method of Tarbell et. al., supra.,), there is obtained 1,1-diphenyl-3-cyclohexyl-;
1,1-diphenyl-3-phenyl-;
1,1-diphenyl-3-benzyl-; and
1,1-diphenyl-3-(p-methoxyphenyl)-3-(2-pyridylethyl)-urea, respectively.

EXAMPLE 5

To a solution of 3.25 gms. (0.03 mole) of 4-aminomethylpyridine in 100 ml. of tetrahydrofuran there is slowly added with stirring 5.70 gm. (0.03 mole) of p-diethylaminophenylisocyanate. The resulting mixture is allowed to stand for about 24 hours at room temperature and then it is refluxed for 10 minutes. Solvent is then stripped to give a residue which is 1-(4-pyridylmethyl)-3-(p-diethylaminophenyl)urea.

Similarly, following the above procedure, but replacing the p-diethylaminophenylisocyanate as used therein with equal molar proportions of p-cyclohexylphenylisocyanate,
p-phenylphenylisocyanate,
p-benzylphenylisocyanate,
m-allylphenylisocyanate,
m-cyanophenylisocyanate,
m-methoxyphenylisocyanate,
p-trifluoromethylphenylisocyanate,
m-diethylaminophenylisocyanate,
p-methylthiophenylisocyanate
p-phenylthiophenylisocyanate, and
p-phenoxyphenylisocyanate, respectively, there is obtained 1-(4-pyridylmethyl)-3-(p-cyclohexylphenyl)urea,
1-(4-pyridylmethyl)-3-(p-biphenyl)urea,
1-(4-pyridylmethyl)-3-(p-benzylphenyl)urea,
1-(4-pyridylmethyl)-3-(m-allylphenyl)urea,
1-(4-pyridylmethyl)-3-(m-cyanophenyl)urea,
1-(4-pyridylmethyl)-3-(m-methoxyphenyl)urea,
1-(4-pyridylmethyl)-3-(p-trifluoromethylphenyl)urea,
1-(4-pyridylmethyl-3-(m-diethylaminophenyl)urea,
1-(4-pyridylmethyl)-3-(p-methylthiophenyl)urea,
1-(4-pyridylmethyl)-3-(p-phenylthiophenyl)urea, and
1-(4-pyridylmethyl)-3-(p-phenoxyphenyl)urea, respectively.

EXAMPLE 6

1-(p-aminophenyl)-3-(4-pyridylmethyl)urea.

To a mixture of 5.72 gms. (0.02 mole) of 1-(p-nitrophenyl)-3-methyl-3methyl-3-(4-pyridylmethyl)urea (see U.S. Pat. No. 3,700,678), 200 ml. of ethanol and 65 ml. of hydrazine hydrate there is added with stirring 0.5 gms. of 5 percent palladium-on-carbon in 50 ml. of ethanol. The resulting mixture is allowed to stand overnight at room temperature and then is refluxed for two to three hours. The hot reaction mixture is then filtered and the filtrate evaporated to remove solvent. The residue is 1-(p-aminophenyl)-3-methyl-3-(4-pyridylmethyl)urea.

EXAMPLE 7

1-(p-acetamidophenyl)-3-methyl-3-(4-pyridylmethyl)urea.

To a chilled (circa 0° C.) solution of 5.12 gms. (0.02 mole) of 1-(p-aminophenyl)-3-methyl-3-(4-pyridylmethyl)urea (Example 6., supra.) in 75 ml. of pyridine there is added dropwise 1.48 gms. (0.02 mole) of acetyl chloride with stirring, while maintaining the temperature of the reaction mixture at circa 0° C. Stirring is continued for 30 minutes and then the reaction mixture is allowed to stand at room temperature overnight. Solvent is stripped and the residue suspended in water. Upon removal of the water there is obtained 1-(p-acetamidophenyl)-3-(4-pyridylmethyl)urea.

EXAMPLE 8

1-(p-ethylaminophenyl)-3-methyl-3-(4-pyridylmethyl)urea

To 2.89 gms. (0.01 mole) of 1-(p-trifluoroacetamidophenyl)-3-methyl-3-(4-pyridylmethyl)urea [prepared by reacting 1-(p-aminophenyl)-3-methyl-3- (4-pyridylmethyl)urea (Example 6., supra.) with trifluoroacetic anhydride (method of Hickenbottom, Reactions of Organic Compounds, Longmans, London, 1963)] there is added 6.24 gms. (0.04 mole) of ethyl iodide in 50 ml. of dry acetone. The acetone is then stripped and the residue added to 50 ml. of water. The aqueous mixture is warmed to reflux for about 30 minutes and then allowed to stand overnight. The mixture is then stripped of water to give 1-(p-ethylaminophenyl)-4-methyl-3-(4-pyridylmethyl)urea.

EXAMPLE 9

1,1-Diphenyl-3-methyl-3-(2-pyridylethyl)urea hydrochloride

The 1,1-diphenyl-3-methyl-3-(2-pyridylethyl)urea obtained in Example 4, supra., is dissolved in 150 ml. of ethanol. To the solution there is added sufficient concentrated hydrochloric acid to acidify the solution to a pH of circa 5, and then the resulting solution is chilled, whereupon a solid precipitates. The precipitate is separated, washed with cold ethanol and dried to give 13.36 gms. (73 percent of theory) based upon starting 2-methylaminoethylpyridine of 1,1-diphenyl-3-methyl-3-(2-pyridylethyl)urea hydrochloride in the form of white crystals.

Similarly, following the above procedure but replacing the 1,1-diphenyl-3-methyl-3-(2-pyridylethyl)urea as used therein with an equal molar proportion of any of the compounds prepared according to Examples 1–8 supra., the corresponding hydrochloride salt is obtained.

EXAMPLE 10

1-(4-pyridylmethyl)-3-phenylurea-N-oxide

To an appropriate reaction vessel there is charged 11.35 gms. (0.05 mole) of 1-(4-pyridylmethyl)-3-phenylurea dissolved in 100 ml. of glacial acetic acid. To the solution there is added 7.5 ml. of 30 percent hydrogen peroxide and the resulting solution is allowed to stand overnight at room temperature. At the end of this period, the mixture is heated circa. 60° C. – 80° C. for about four hours. The mixture is then evaporated to dryness and the residue mixed with water. The resulting mixture is evaporated to remove water, leaving a viscous liquid which solidifies upon standing. The solid is suspended in 200 ml. of water and filtered. The filtrate is neutralized to a pH of 7 with sodium carbonate whereupon a precipitate appears. The precipitate is separated, washed with water and crystallized from absolute ethanol to give 2.11 gms. (18 percent of theory) of 1-(4-pyridylmethyl)-3-phenylurea-N-oxide in the form of fine white crystals, m.p. 174.1° C.

EXAMPLE 11

1-(2-nitrophenyl)-3-(2-pyridylethyl)urea-N-oxide

Following the procedure of Example 10., supra., but replacing the 1-(4-pyridylmethyl)-3-phenylurea as used therein with 14.30 gms. (0.05 mole) of 1-(2-nitrophenyl)-3-(2-pyridylethyl)urea, there is obtained 9.39 gms. (62 percent yield) of 1-(2-nitrophenyl-3-(2-pyridylethyl)urea-N-oxide in the form of bright yellow feathery crystals, m.p. 182.0° C.

EXAMPLE 12

1,1-Diphenyl-3-(2-pyridylethyl)urea-N-oxide

Following the procedure of Example 10, supra., but replacing the 1-(4-pyridylmethyl)-3-phenylurea as used therein with 15.85 gms. (0.05 mole) of 1,1-diphenyl-3-(2-(2-pyridylethyl)urea (Example 3, supra.) there is obtained 6.88 gms. (42 percent of theory) of 1,1-diphenyl-3-(2-pyridylethyl)urea-N-oxide in the form of gray-brown crystals, m.p. 139.4° C.

Similarly, repeating the above procedure but replacing the 1,1-diphenyl-3-(2-pyridylethyl)urea as used therein with an equal molar proportion of any compound of the formula (I) or acid salt thereof such as those prepared according to Examples 1 to 9, supra., and the acid addition salts thereof, the corresponding N-oxide is obtained.

The following examples illustrate the compositions and uses of the compounds of the invention and the method of the invention.

EXAMPLE 13

Tablets

One thousand tablets for oral use, each containing 250 mg. of 1,1-diphenyl-3-(3-pyridylmethyl)urea as the essential active ingredient are prepared from the following ingredients:

| | |
|---|---|
| 1,1-diphenyl-3-(pyridylmethyl)urea | 250 gms. |
| lactose | 200 gms. |
| microcrystalline cellulose N.F. | 50 gms. |
| starch | 5 gms. |
| magnesium stearate powder | 1 gm. |

The ingredients are thoroughly mixed and slugged. The slugs are broken down by forcing through a screen and the resulting granules are then compressed into tablets.

These tablets are useful in controlling atonic uterine hemorrhage in adult humans when given at a dose of 1 to 6 tablets. High blood levels of $PGF_2\alpha$ and $PGE_2$ are observed for from 6 to 8 hours after administration.

The tablets are also useful for treating male mammals for infertility when 1 to 3 tablets are given 3 to 4 times a week.

EXAMPLE 14

Capsules

One thousand two-piece hard gelatine capsules for oral use, each capsule containing 250 mg. of 1,1-diphenyl-3-(2-pyridylethyl)urea (Example 3, supra., are prepared from the following ingredients:

| | |
|---|---|
| 1,1-diphenyl-3-(2-pyridylethyl)urea | 250 gms. |
| lactose | 200 gms. |
| talc | 25 gms. |
| magnesium stearate | 2 gms. |

The finely powdered materials are mixed thoroughly, then filled into hard gelatin capsules of appropriate size. The capsules are given to adult humans suffering from burns at a dose of 1 to 3 capsules given 3 to 14 times a week, resulting in an acceleration of healing and epidermal proliferation.

EXAMPLE 15

Aqueous solution

An aqueous oral preparation containing in each teaspoonful (5 ml.) 500 mg. of essential active ingredient is prepared from the following:

| | | |
|---|---|---|
| 1,1-diphenyl-3-methyl-3-(2-pyridyl-ethyl)urea hydrochloride (Example 5, supra.) | 500 | gms. |
| glycerin | 2000 | ml. |
| tragacanth powder | 50 | gms. |
| propylparaben | 3 | gms. |
| sucrose | 6.5 | gms. |
| orange oil flavor | 5 | gms. |
| deionized water q.s. | 5000 | ml. |

The above oral preparations may be given to adult humans at a dose of 1 to 4 teaspoons 3 to 14 times weekly to accelerate the healing of epidermal wounds.

EXAMPLE 16

Injectable

A sterile suspension suitable for intramuscular injection and containing in each milliliter 250 mg. of 1-(4-pyridylmethyl)-3-(2,5-dimethylphenyl)urea is prepared from the following ingredients:

| | | |
|---|---|---|
| 1-(4-pyridylmethyl)-3-(2,5-dimethyl-phenyl)urea | 250 | gms. |
| benzyl benzoate | 200 | ml. |
| methylparaben | 1.5 | gms. |
| propylparaben | 0.5 | gms. |
| cottonseed oil q.s. | 1000 | ml. |

The above sterile injectable is useful in controlling the developement of thrombi following saphenectomy when given at a dose of 1 to 4 ml. administered 2 to 6 hours prior to said saphenectomy.

EXAMPLE 17

Suppository

One thousand suppositories, each weighing 4.0 gms. and containing 500 mg. of 1,1-diphenyl-3-(2-pyridylethyl)urea-N-oxide (Example 10, supra.) as the essential active ingredient are prepared from the following ingredients:

| | | |
|---|---|---|
| 1,1-diphenyl-3-(2-pyridylethyl)-urea-N-oxide | 500 | gms. |
| propylene glycol | 2000 | gms. |
| polyethylene glycol 4000 | 1000 | gms. |
| polyethylene glycol 400 | 500 | gms. |

The 1,1-diphenyl-3-(2-pyridylethyl)urea N oxide is added to the propylene glycol and the mixture milled until uniformly dispersed. The polyethylene glycol 4000 and polyethylene glycol 400 are melted together and the propylene glycol dispersion added. The suspension is poured into molds and allowed to cool and solidify.

These suppositories are useful for controlling development of thrombi in mammals when given rectally at a dose of 1 suppository 3 to 7 times a week.

EXAMPLE 18

Various compounds of the formula (I) are admixed with water and administered orally to groups of 5 male Carworth rats (weighing 250–275 gms. each) at a dosage of 60 mg. per kilogram of body weight. The rats are prepared by fasting overnight (16 hours) prior to administration. About 3 hours after administration, tails are clipped and the rats bled. 5 ml. of blood is collected in citrated syringes (0.1 ml. of 3.8 percent w/v sodium citrate per ml. of whole blood). The collected blood is centrifuged at 900 rpm for 15 minutes and the platelet rich plasma separated and pooled for each group of 5 rats. For each 1.0 mls. of pooled plasma there is added 0.5 ml. of 0.15M sodium phosphate buffer (pH 7.4). The resulting mixture is allowed to stand at room temperature for 30 minutes and then 0.5 mls. of sodium fluoride (4 mgs./ml. aqueous solution) is added. The mixture is then incubated at 37° C. for sixty minutes, cooled under running tap water and centrifuged at 2500 rpm for 20 minutes. The supernatant solution is separated and analyzed for $PGF_2\alpha$ concentration by the method of Kirton et al., Biochemical and Biophysical Res. Comm. Volumn 47, 903 (1972).

The compounds employed and the results obtained are given in Table I below. Group A does not represent the invention but is a control group of 5 rats which did not receive an administration of a compound (I).

TABLE I

| Group | Compound (I) Administered | Concentration of $PGF_2\alpha$ Found (ng./ml.) |
|---|---|---|
| A (Control) | None | 33.8 ± 4.2 |
| B | 1-(4-pyridylmethyl)-3-(4-chlorophenyl)urea | 45.8 ± 4.3 |
| C | 1-(4-pyridylmethyl)-3-(2-fluorophenyl)urea | 157.2 ± 14.6 |

Similarly, repeating the above procedure but replacing the compounds of formula (I) as used therein with any other compounds of the formula (I), or of the formula (XI) and the pharmaceutically acceptable acid addition salts thereof such as for example:

1-(2-pyridylmethyl)-3-phenylurea,
1-(2-pyridylethyl)-3-(4-methoxyphenyl)urea,
1-[2-(3-methyl)pyridyl-(methyl)]-3-phenylurea,
1-methyl-1-(2-pyridylmethyl)-3-phenylurea,
1-methyl-1-(2-pyridylmethyl)-3-(3-nitrophenyl)urea
1-methyl-1-(2-pyridylmethyl)-3-(3-trifluoromethylphenyl)urea,
1-methyl-1-(3-pyridylmethyl)-3-(3,4-dimethylphenyl)urea,
1-methyl-1-(4-pyridylmethyl)-3-(4-ethoxy-phenyl)urea,
the like and such as those prepared according to Example 1–12, supra., similar observations of increased prostaglandin production are made.

A further group of compounds of the invention are those compounds of Formula I wherein $R_1$, $R_5$ and $R_6$ are hydrogen; $R_2$ is selected from the group consisting of hydrogen, halogen, alkyl of one to four carbon atoms, inclusive, alkoxy of one to four carbon atoms, inclusive, and trifluoromethyl; $R_3$ and $R_4$ are the same or different and are selected from the group consisting of hydrogen, alkyl of one to four carbon atoms, inclusive, and phenyl; $R_7$ is selected from the group consisting of hydrogen, halogen, alkyl of one to four carbon atoms, inclusive, alkoxy of one to four carbon atoms, inclusive, trifluoromethyl, and nitro; n is one or two; provided that when R₇ is chloro, the pyridine ring moiety is attached to the alkylene at the 4-carbon position; and further provided that when R₂ is hydrogen or alkyl of one to four carbon atoms, inclusive, then R₇ is trifluoromethyl or nitro and R₄ is phenyl.

The N-oxides of the above-identified group are also within the scope of this invention. The groupings of compounds are useful in the same manner as the previous generic groupings and are formulated into like compositions.

We claim:

1. A compound selected from those of formula:

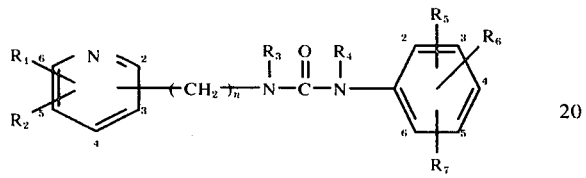

and a pharmaceutically acceptable acid addition salt thereof wherein $R_1$ and $R_2$ are each selected from the group consisting of hydrogen, halogen, alkyl of one to six carbon atoms, inclusive, cycloalkyl of three to six carbon atoms, inclusive, alkenyl of two to six carbon atoms, inclusive, phenyl, alkoxy of one to twelve carbon atoms, inclusive, nitro, amino, alkylamino with alkyl of one to twelve carbon atoms, inclusive, dialkylamino with each alkyl having one to twelve carbon atoms, inclusive, acylamino with the acyl group being alkyl of one to twelve carbon atoms, inclusive, and trihalomethyl;

$R_3$ and $R_4$ are each selected from the group consisting of hydrogen, alkyl of one to four carbon atoms, inclusive, cycloalkyl of three to four carbon atoms, inclusive, aryl of six to twelve carbon atoms, inclusive, aralkyl of seven to twelve carbon atoms, inclusive, and aryl of six to twelve carbon atoms, inclusive, substituted with a group selected from halogen, alkoxy of one to four carbon atoms, inclusive, nitro, aryloxy with aryl of six to twelve carbon atoms, inclusive alkyl of one to twelve carbon atoms, inclusive, cycloalkyl of three to eight carbon atoms, inclusive, alkenyl of two to twelve carbon atoms, inclusive, aryl of six to twelve carbon atoms, inclusive, and aralkyl of seven to twelve carbon atoms, inclusive;

$R_5$ is selected from the group consisting of hydrogen, fluoro, chloro, bromo, iodo, alkyl of one to twelve carbon atoms, inclusive, cycloalkyl of three to eight carbon atoms, inclusive alkenyl of two to twelve carbon atoms, inclusive, aryl of six to twelve carbon atoms, inclusive, aralkyl of seven to twelve carbon atoms, inclusive, alkoxy of one to twelve carbon atoms, inclusive, halogen substituted alkyl of one to twelve carbon atoms, inclusive, halogen substituted cycloalkyl of three to eight carbon atoms, inclusive, halogen substituted alkenyl of two to twelve carbon atoms, inclusive, halogen substituted aryl of six to twelve carbon atoms, inclusive, and halogen substituted aralkyl of seven to twelve carbon atoms, inclusive;

$R_6$ and $R_7$ are each selected from the group consisting of nitro, amino, acylamino with acyl being alkyl of one to twelve carbon atoms, inclusive, alkylamino with alkyl of one to twelve carbon atoms, inclusive, dialkylamino with each alkyl of one to twelve carbon atoms, inclusive, aryloxy with aryl of six to twelve carbon atoms, inclusive, and a group $R_5$ as previously defined: and n is an integer of from 1 to 2, inclusive; provided that when one of $R_5$, $R_6$ and $R_7$ is chlorine, the pyridine ring moiety of said compound is attached to the rest of the molecule through the pyridyl ring carbon atom at the four carbon position; and further provided that when $R_1$ and $R_2$ are both selected from the group consisting of hydrogen and alkyl of one to six carbon atoms, inclusive, said compound is selected from those wherein $R_7$ is selected from the group consisting of cycloalkyl of three to eight carbon atoms, inclusive, aryl of six to twelve carbon atoms, inclusive, aralkyl of seven to twelve carbon atoms, inclusive, alkenyl of two to twelve carbon atoms, inclusive, amino, acylamino with acyl being alkyl from one to twelve carbon atoms, inclusive, alkylamino with alkyl of one to twelve carbon atoms, inclusive, dialkylamino with each alkyl being one to twelve carbon atoms, inclusive, and aryloxy with aryl of six to twelve carbon atoms, inclusive; and those compounds wherein $R_4$ is selected from the group consisting of cycloalkyl of three to six carbon atoms, inclusive, aryl of six to twelve carbon atoms, inclusive, aralkyl of seven to twelve carbon atoms, inclusive, and aryl substituted with a group selected from the group consisting of halogen, alkoxy of one to four carbon atoms, inclusive, nitro, aryloxy with aryl of six to twelve carbon atoms, inclusive, alkyl of one to twelve carbon atoms, inclusive, cycloalkyl of three to eight carbon atoms, inclusive, alkenyl of two to twelve carbon atoms, inclusive, aryl of six to twelve carbon atoms, inclusive, and aralkyl of seven to twelve carbon atoms, inclusive.

2. A compound in accordance with claim 1 wherein $R_1$, $R_5$ and $R_6$ are hydrogen; $R_2$ is selected from the group consisting of hydrogen, halogen, alkyl of one to four carbon atoms, inclusive, alkoxy of one to four carbon atoms, inclusive, and trifluoromethyl; $R_3$ and $R_4$ are the same or different and are selected from the group consisting of hydrogen, alkyl of one to four carbon atoms, inclusive, and phenyl; $R_7$ is selected from the group consisting of hydrogen, fluoro, chloro, bromo, iodo, alkyl of one to four carbon atoms, inclusive, alkoxy of one to four carbon atoms, inclusive, trifluoromethyl, and nitro; n is one to two, provided that when $R_7$ is chloro, the pyridine ring moiety is attached to the alkylene at the 4-carbon position; and further provided that when $R_2$ is hydrogen or alkyl of one to four carbon atoms, inclusive, then $R_7$ is trifluoromethyl or nitro and $R_4$ is phenyl.

3. The compound of claim 1 which is 1,1-diphenyl-3-(3-pyridylmethyl)urea.

4. The compound of claim 1 which is 1,1-diphenyl-3-(4-pyridylmethyl)urea.

5. The compound of claim 1 which is 1,1-diphenyl-3-(2-pyridylethyl)urea.

6. The compound of claim 1 which is 1,1-diphenyl-3-methyl-3-(2-pyridylethyl)urea.

7. The compound of claim 1 which is 1,1-diphenyl-3-methyl-3-(2-pyridylethyl)urea hydrochloride.

8. A compound selected from those of the formula:

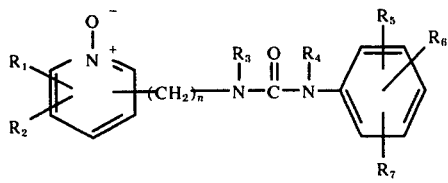

and a pharmaceutically acceptable acid addition salt thereof wherein $R_1$ and $R_2$ are each selected from the group consisting of hydrogen, halogen, alkyl of one to six carbon atoms, inclusive, cycloalkyl of three to six carbon atoms, inclusive, alkenyl of two to six carbon atoms, inclusive, phenyl, alkoxy of one to twelve carbon atoms, inclusive, nitro, amino, alkylamino with alkyl of one to twelve carbon atoms, inclusive, dialkylamino with each alkyl of one to twelve carbon atoms, inclusive, acylamino with acyl being alkyl of one to twelve carbon atoms, inclusive, and trihalomethyl;

$R_3$ and $R_4$ are each selected from the group consisting of hydrogen, alkyl of one to four carbon atoms, inclusive, cycloalkyl of three to four carbon atoms, inclusive, aryl of six to twelve carbon atoms, inclusive, aralkyl of seven to twelve carbon atoms, inclusive, and aryl of six to twelve carbon atoms, inclusive, substituted with a group selected from the group consisting of halogen, alkoxy of one to four carbon atoms, inclusive, nitro, aryloxy with aryl of six to twelve carbon atoms, inclusive, alkyl of one to twelve carbon atoms, inclusive, cycloalkyl of three to eight carbon atoms, inclusive, alkenyl of two to twelve carbon atoms, inclusive, aryl of six to twelve carbon atoms, inclusive, and aralkyl of seven to twelve carbon atoms, inclusive;

$R_5$ is selected from the group consisting of hydrogen, fluoro, chloro, bromo, iodo, alkyl of one to twelve carbon atoms, inclusive, cycloalkyl of three to eight carbon atoms, inclusive, alkenyl of two to twelve carbon atoms, inclusive, aryl of six to twelve carbon atoms, inclusive, aralkyl of seven to twelve carbon atoms, inclusive, alkoxy of one to twelve carbon atoms, inclusive, halogen substituted alkyl of one to twelve carbon atoms, inclusive, halogen substituted cycloalkyl of three to eight carbon atoms, inclusive, halogen substituted alkenyl of two to twelve carbon atoms, inclusive, halogen substituted aryl of six to twelve carbon atoms, inclusive, and halogen-substituted aralkyl of seven to twelve carbon atoms, inclusive;

$R_6$ and $R_7$ are each selected from the group consisting of nitro, amino, acylamino with acyl being alkyl of one to twelve carbon atoms, inclusive, alkylamino with alkyl of one to twelve carbon atoms, inclusive, dialkylamino with each alkyl of one to twelve carbon atoms, inclusive, aryloxy with aryl of six to twelve carbon atoms, inclusive, and a group $R_5$ as previously defined; and n is an integer of from 1 to 2, inclusive; provided that when one of $R_5$, $R_6$ and $R_7$ is chloro, the pyridine ring moiety of said compound is attached to the rest of the molecule through the pyridyl ring carbon atom at the 4-carbon position.

9. The compound of claim 9 which is 1-(2-nitrophenyl)-3-(2-pyridylethyl)urea-N-oxide.

10. The compound of claim 8 which is 1,1-diphenyl-3-(2-pyridylethyl)urea-N-oxide.

11. The compound of claim 8 which is 1-(4-pyridylmethyl)-3-phenylurea-N-oxide.

* * * * *

UNITED STATES PATENT OFFICE
CERTIFICATE OF CORRECTION

Patent No. 4,001,256      Dated 4 January 1977

Inventor(s) William A. Callahan, et al.

It is certified that error appears in the above-identified patent and that said Letters Patent are hereby corrected as shown below:

Column 9, line 65, "(IV) are" should read -- (VI) are --;
Column 16, line 22, "methyl(P3-nitro-" should read -- methyl(3-nitro- --; line 25, "1-methyl-3-(3-" should read -- 1-methyl-1-(3- --;
Column 17, line 23, "1,1-diphenyl-3-[2-(4-diethylaminopyridyl)methyl-]urea, diethylaminopyridyl)-methyl]urea," should read -- 1,1-diphenyl-3-[2-(4-diethylaminopyridyl)methyl]urea, --;
Column 18, line 23, "p-phenylithiophenylisocyanate" should read -- p-phenylthiophenylisocyanate --;
Column 20, lines 8-9, "1,1-diphenyl-3-(2-(2-" should read -- 1,1-diphenyl-3-(2- --;
Column 26, line 31, "compound of claim 9" should read -- compound of claim 8 --.

Signed and Sealed this

First Day of September 1981

[SEAL]

Attest:

GERALD J. MOSSINGHOFF

Attesting Officer      Commissioner of Patents and Trademarks